United States Patent
Ach et al.

(10) Patent No.: US 11,535,889 B2
(45) Date of Patent: Dec. 27, 2022

(54) USE OF TRANSPOSASE AND Y ADAPTERS TO FRAGMENT AND TAG DNA

(71) Applicant: AGILENT TECHNOLOGIES, INC., Santa Clara, CA (US)

(72) Inventors: Robert A. Ach, San Francisco, CA (US); Nicholas M. Sampas, San Jose, CA (US); Brian Jon Peter, Los Altos, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 965 days.

(21) Appl. No.: 16/295,838

(22) Filed: Mar. 7, 2019

(65) Prior Publication Data
US 2019/0194737 A1    Jun. 27, 2019

Related U.S. Application Data

(62) Division of application No. 15/407,998, filed on Jan. 17, 2017, now abandoned.

(60) Provisional application No. 62/316,385, filed on Mar. 31, 2016.

(51) Int. Cl.
| | |
|---|---|
| *C12Q 1/6855* | (2018.01) |
| *C12Q 1/6806* | (2018.01) |
| *C12Q 1/6848* | (2018.01) |
| *C12Q 1/6874* | (2018.01) |
| *C12Q 1/6869* | (2018.01) |

(52) U.S. Cl.
CPC ......... *C12Q 1/6855* (2013.01); *C12Q 1/6806* (2013.01); *C12Q 1/6848* (2013.01); *C12Q 1/6869* (2013.01); *C12Q 1/6874* (2013.01)

(58) Field of Classification Search
CPC combination set(s) only.
See application file for complete search history.

(56) References Cited

U.S. PATENT DOCUMENTS

| | | |
|---|---|---|
| 6,287,825 B1 | 9/2001 | Weissman et al. |
| 2006/0292597 A1 | 12/2006 | Shapero et al. |
| 2010/0120098 A1 | 5/2010 | Grunenwald et al. |
| 2012/0208724 A1 | 8/2012 | Steemers et al. |
| 2012/0301925 A1 | 11/2012 | Belyaev |
| 2013/0203605 A1 | 8/2013 | Shendure et al. |
| 2014/0093916 A1 | 4/2014 | Belyaev |
| 2015/0176071 A1 | 6/2015 | Fisher et al. |
| 2015/0368638 A1 | 12/2015 | Steemers |

FOREIGN PATENT DOCUMENTS

| | | |
|---|---|---|
| CN | 102796728 A | 11/2012 |
| CN | 103443338 A | 12/2013 |
| CN | 104797718 A | 7/2015 |
| CN | 105102697 A | 11/2015 |
| WO | 2012061832 A1 | 5/2012 |
| WO | 2012106546 A2 | 8/2012 |
| WO | 2015095226 A2 | 6/2015 |
| WO | 2015189636 A1 | 12/2015 |
| WO | 2016003814 A1 | 1/2016 |
| WO | 2016061517 A2 | 4/2016 |
| WO | 2016168351 A1 | 10/2016 |

OTHER PUBLICATIONS

Extended European Search Report dated Nov. 5, 2019, Application No. 17776044.4, 5 pages.
Buenrostro, Jason D. et al., "Transposition Of Native Chromatin For Multimodal Regulatory Analysis And Personal Epigenomics," Nat Methods, vol. 10, No. 12, pp. 1213-1218, Dec. 2013, 15 pages.
Gohl, Daryl M. et al., "Large-Scale Mapping of Transposable Element Insertion Sites Using Digital Encoding of Sample Identity," Genetics, vol. 196, pp. 615-623, Mar. 2014, 15 pages.
Picelli, Simone et al., "Tn5 Transposase And Tagmentation Procedures For Massively-Scaled Sequencing Projects," Genome Research, http://genome.cshlp.org/content/suppl/2014/10/06/gr.177881.114. DC1, Jul. 30, 2014, 32 pages.
Bhasin, et al., "Hairpin Formation in Tn5 Transposition", The Journal Of Biological Chemistry, vol. 274, No. 52, Dec. 24, 1999, 37021-37029.
Caruccio, et al., "NexteraTM Technology for NGS DNA Library Preparation: Simultaneous Fragmentation and Tagging by In Vitro Transposition", NexteraTM Technology, vol. 16, No. 3, 2009, 4-6.
International Search Report and Written Opinion dated Mar. 23, 2017, Application No. PCT/US2017/014183, 18 pages.
Reznikoff, et al., "Comparative Sequence Analysis of IS50/Tn5 Transposase", Journal of Bacteriology, vol. 186, No. 24, Dec. 2004, 8240-8247.

*Primary Examiner* — Jennifer Dunston

(57) ABSTRACT

Described herein is an adapter comprising a population of first oligonucleotides, a second oligonucleotide and a third oligonucleotide, wherein the first oligonucleotides, the second oligonucleotide and the third oligonucleotide are hybridized together to produce a complex that comprises: (i) a first end comprising a transposase recognition sequence, (ii) a central single-stranded region of variable sequence and (iii) a second end comprising sequences that are non-complementary. A method, as well as a kit for practicing the method, are also provided.

13 Claims, 6 Drawing Sheets

Specification includes a Sequence Listing.

USE OF TRANSPOSASE AND Y ADAPTERS TO FRAGMENT AND TAG DNA

CROSS-REFERENCING

This patent application is a divisional of U.S. patent application Ser. No. 15/407,998, filed on Jan. 17, 2017, and claims the benefit of U.S. provisional application Ser. No. 62/316,385, filed on Mar. 31, 2016, which applications are incorporated by reference in their entireties.

REFERENCE TO SEQUENCE LISTING

The computer-readable Sequence Listing submitted on Mar. 7, 2019 and identified as follows: 1180 bytes ASCII (Text) file named "20160021-06_Sequence_Listing.txt," created Mar. 5, 2019, is incorporated herein by reference in its entirety.

BACKGROUND

Next-generation Sequencing (NGS) technologies have made whole-genome sequencing (WGS) routine, and various target enrichment methods have enabled researchers to focus sequencing power on the most important regions of interest. However, there is still a need for better methods for making NGS sequencing libraries. For example, genomic DNA can be prepared for next-generation sequencing (NGS) by "tagmentation", where the transposase causes staggered double-stranded breaks in the genomic DNA and simultaneously inserts small oligonucleotide tags on the ends. However, one problem with this method is that it requires that there be different tags on the two ends of any particular fragment after tagmentation in order to get PCR amplification, since fragments with the same sequences at both ends will not adequately PCR due to suppression PCR effects. However, in many methods, in order to get different sequences on the ends of a fragment, two different sequences must be loaded onto the transposase before tagmentation. Since each end gets randomly tagged, there is a 50% chance that both ends of a fragment will have the same sequence added. These fragments then get lost in PCR and/or sequencing.

Further, all sequencing methods result in sequence reads that contain errors, e.g., PCR errors and sequencing errors. Some errors can be corrected, but when the amount of sample is limiting (e.g., when there are only a handful of mutant molecules relative to non-mutant molecules) it is often impossible to determine out whether a variation in a sequence is caused by an error or if it is a "real" mutation.

SUMMARY

Described herein, among other things, is an adapter comprising a population of first oligonucleotides, a second oligonucleotide and a third oligonucleotide, wherein the first oligonucleotides, the second oligonucleotide and the third oligonucleotide are hybridized together to produce a complex that comprises: (i) a first end comprising a transposase recognition sequence, (ii) a central single-stranded region of variable sequence and (iii) a second end comprising sequences that are non-complementary.

Also described herein, among other things, is method for tagmenting a sample, comprising: contacting a sample comprising double-stranded DNA with a transposase loaded with the present adaptor; and filling in and sealing the central single-stranded region of the adaptor using a polymerase and ligase, thereby producing a population of DNA fragments that are tagged at both ends by a Y adaptor each comprising the variable sequence of a first oligonucleotide on both strands.

Kits for practicing the method are also provided. In certain embodiments, a kit may comprise a transposase; the present adaptor; and a polymerase.

The compositions, methods and kits described herein find particular use in analyzing samples of DNA in which the amount of DNA is limited and that contain fragments having a low copy number mutation (e.g. a sequence caused by a mutation that is present at low copy number relative to sequences that do not contain the mutation). In such samples, the mutant sequences may only be present at a very limited copy number (e.g., less than 10 in a background of hundreds or thousands of copies of the wild type sequence) and there is a need for those sequences to be efficiently captured and tagged in a way that adds the same molecular barcode to both strands of each tagged molecule. True mutations should be at the same positions in both strands and, as such, the ability to add the same barcode to both strands of an initial double-stranded molecule allows the sequence reads derived from both strands of the initial molecule to be identified and compared. The confidence that a potential sequence variation is a true variation (rather than a PCR or sequencing error) increases if it is present in both strands of the same molecule.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
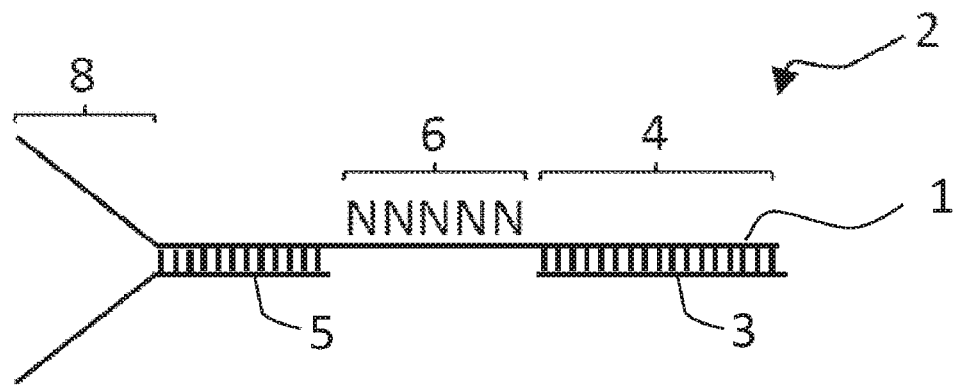
FIG. 1 schematically illustrates some of the features of the present adaptor.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. In one embodiment, the term as used in its broadest sense, refers to any plant, animal or viral material containing DNA or RNA, such as, for example, tissue or fluid isolated from an individual (including without limitation plasma, serum, cerebrospinal fluid, lymph, tears, saliva and tissue sections), from preserved tissue (such as FFPE sections) or from in vitro cell culture constituents, as well as samples from the environment.

The term "nucleic acid sample," as used herein denotes a sample containing nucleic acids. A nucleic acid samples used herein may be complex in that they contain multiple different molecules that contain sequences. Genomic DNA samples from a mammal (e.g., mouse or human) are types of complex samples. Complex samples may have more than $10^4$, $10^5$, $10^6$ or $10^7$ different nucleic acid molecules. Also, a complex sample may comprise only a few molecules, where the molecules collectively have more than $10^4$, $10^5$, $10^6$ or $10^7$ or more nucleotides. A DNA target may originate from any source such as genomic DNA, or an artificial DNA construct. Any sample containing nucleic acid, e.g., genomic DNA made from tissue culture cells or a sample of tissue, may be employed herein.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order). A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 11 to 30, 31 to 40, 41 to 50, 51-60, 61 to 70, 71 to 80, 80 to 100, 100 to 150 or 150 to 200 nucleotides in length, for example.

The term "primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with their use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

The term "hybridization" or "hybridizes" refers to a process in which a nucleic acid strand anneals to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42° C. in 50% formamide, 5×SSC, 5×Denhardt's solution, 0.5% SDS and 100 ug/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule may include denaturing the template nucleic acid, annealing primers to the template nucleic acid at a temperature that is below the melting temperatures of the primers, and enzymatically elongating from the primers to generate an amplification product. The denaturing, annealing and elongating steps each can be performed one or more times. In certain cases, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "covalently linking" refers to the production of a covalent linkage between two separate molecules, e.g., the top and bottom strands of a double stranded nucleic acid. Ligating is a type of covalent linking.

The term "genotyping", as used herein, refers to any type of analysis of a nucleic acid sequence, and includes sequencing, polymorphism (SNP) analysis, and analysis to identify rearrangements.

The term "sequencing", as used herein, refers to a method by which the identity of at least 10 consecutive nucleotides (e.g., the identity of at least 20, at least 50, at least 100 or at least 200 or more consecutive nucleotides) of a polynucleotide are obtained.

The term "next-generation sequencing" refers to the so-called parallelized sequencing-by-synthesis or sequencing-by-ligation platforms currently employed by Illumina, Life Technologies, Pacific Bio, and Roche etc. Next-generation sequencing methods may also include nanopore sequencing methods or electronic-detection based methods such as Ion Torrent technology commercialized by Life Technologies.

The term "extending", as used herein, refers to the extension of a primer by the addition of nucleotides using a polymerase. If a primer that is annealed to a nucleic acid is extended, the nucleic acid acts as a template for extension reaction.

The term "barcode sequence" or "molecular barcode", as used herein, refers to a unique sequence of nucleotides can be used to a) identify and/or track the source of a polynucleotide in a reaction, b) count how many times an initial molecule is sequenced and c) pair sequence reads from different strands of the same molecule. Barcode sequences may vary widely in size and composition; the following references provide guidance for selecting sets of barcode sequences appropriate for particular embodiments: Casbon (Nuc. Acids Res. 2011, 22 e81), Brenner, U.S. Pat. No. 5,635,400; Brenner et al, Proc. Natl. Acad. Sci., 97: 1665-1670 (2000); Shoemaker et al, Nature Genetics, 14: 450-456 (1996); Morris et al, European patent publication 0799897A1; Wallace, U.S. Pat. No. 5,981,179; and the like. In particular embodiments, a barcode sequence may have a length in range of from 2 to 36 nucleotides, or from 6 to 30 nucleotides, or from 8 to 20 nucleotides.

In some cases, a barcode may contain a "degenerate base region" or "DBR", where the terms "degenerate base region" and "DBR" refers to a type of molecular barcode that has complexity that is sufficient to help one distinguish between fragments to which the DBR has been added. In some cases, substantially every tagged fragment may have a different DBR sequence. In these embodiments, a high complexity DBR may be used (e.g., one that is composed of at least 10,000 or 100,000, or more sequences). In other embodiments, some fragments may be tagged with the same DBR sequence, but those fragments can still be distinguished by the combination of i. the DBR sequence, ii. the sequence of the fragment, iii. the sequence of the ends of the fragment, and/or iv. the site of insertion of the DBR into the fragment. In some embodiments, at least 95%, e.g., at least 96%, at least 97%, at least 98%, at least 99% or at least 99.5% of the target polynucleotides become associated with a different DBR sequence. In some embodiments a DBR may comprise one or more (e.g., at least 2, at least 3, at least 4, at least 5, or 5 to 30 or more) nucleotides selected from R, Y, S, W, K, M, B, D, H, V, N (as defined by the IUPAC code). In some cases, a double-stranded barcode can be made by making an oligonucleotide containing degenerate sequence (e.g., an oligonucleotide that has a run of 2-10 or more "Ns") and then copying the complement of the barcode onto the other strand, as described below.

Oligonucleotides that contain a variable sequence, e.g., a DBR, can be made by making a number of oligonucleotides separately, mixing the oligonucleotides together, and by amplifying them en masse. In other words, the population of oligonucleotides that contain a variable sequence can be made as a single oligonucleotide that contains degenerate positions (i.e., positions that contain more than one type of nucleotide). Alternatively, such a population of oligonucleotides can be made by fabricating them individually or using an array of the oligonucleotides using in situ synthesis methods, cleaving the oligonucleotides from the substrate and optionally amplifying them. Examples of such methods are described in, e.g., Cleary et al (Nature Methods 2004 1: 241-248) and LeProust et al (Nucleic Acids Research 2010 38: 2522-2540).

In some cases, a barcode may be error correcting. Descriptions of exemplary error identifying (or error correcting) sequences can be found throughout the literature (e.g., in are described in US patent application publications US2010/0323348 and US2009/0105959 both incorporated herein by reference). Error-correctable codes may be necessary for quantitating absolute numbers of molecules. Many reports in the literature use codes that were originally developed for error-correction of binary systems (Hamming codes, Reed Solomon codes etc.) or apply these to quaternary systems (e.g. quaternary Hamming codes; see Generalized DNA barcode design based on Hamming codes, Bystrykh 2012 PLoS One. 2012 7: e36852).

In some embodiments, a barcode may additionally be used to determine the number of initial target polynucleotide molecules that have been analyzed, i.e., to "count" the number of initial target polynucleotide molecules that have been analyzed. PCR amplification of molecules that have been tagged with a barcode can result in multiple sub-populations of products that are clonally-related in that each of the different sub-populations is amplified from a single tagged molecule. As would be apparent, even though there may be several thousand or millions or more of molecules in any of the clonally-related sub-populations of PCR products and the number of target molecules in those clonally-related sub-populations may vary greatly, the number of molecules tagged in the first step of the method can be estimated by counting the number of DBR sequences associated with a target sequence that is represented in the population of PCR products. This number is useful because, in certain embodiments, the population of PCR products made using this method may be sequenced to produce a plurality of sequences. The number of different barcode sequences that are associated with the sequences of a target polynucleotide can be counted, and this number can be used (along with, e.g., the sequence of the fragment, the sequence of the ends of the fragment, and/or the site of insertion of the DBR into the fragment) to estimate the number of initial template nucleic acid molecules that have been sequenced.

The terms "sample identifier sequence" or "sample index" refer to a type of barcode that can be appended to a target polynucleotide, where the sequence identifies the source of the target polynucleotide (i.e., the sample from which sample the target polynucleotide is derived). In use, each sample is tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences.

The term "strand" as used herein refers to a nucleic acid made up of nucleotides covalently linked together by covalent bonds, e.g., phosphodiester bonds. In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure. The nucleotide sequences of the first strand of several exemplary mammalian chromosomal regions (e.g., BACs, assemblies, chromosomes, etc.) is known, and may be found in NCBI's Genbank database, for example.

The term "top strand," as used herein, refers to either strand of a nucleic acid but not both strands of a nucleic acid. When an oligonucleotide or a primer binds or anneals "only to a top strand," it binds to only one strand but not the other. The term "bottom strand," as used herein, refers to the strand that is complementary to the "top strand." When an oligonucleotide binds or anneals "only to one strand," it binds to only one strand, e.g., the first or second strand, but not the other strand.

The terms "reverse primer" and "forward primer" refer to primers that hybridize to different strands in a double-stranded DNA molecule, where extension of the primers by a polymerase is in a direction that is towards the other primer.

The term "both ends of a fragment", as used herein, refers to both ends of a double stranded DNA molecule (i.e., the left hand end and the right hand end if the molecule is drawn out horizontally).

The term "the sequence of a barcode", as used herein, refers to the sequence of nucleotides that makes up the barcode. The sequence of a barcode may be at lest 3 nucleotides in length, more usually 5-30 or more nucleotides in length.

The term "match", as used herein, refers to an action in which two sequences are compared and if they are identical, complementary, or very similar (e.g., when error correcting barcodes are used) they are indicated as being a match. In some embodiments, matched sequences are placed into a group.

The term "or variant thereof", used herein, refers to a protein that has an amino acid sequence that at least 80%, at least 85%, at least 90%, at least 95%, at least 97%, at least 98% or at least 99% identical to a protein that has a known activity, wherein the variant has at least some of the same activities as the protein of known activity. For example, a variant of a wild type transposase should be able to catalyze the insertion of a corresponding transposon into DNA.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., Mg') may also be present. PCR reagents may optionally contain a template from which a target sequence can be amplified.

The term "adjacent to" refers to a distance of less than the longest dimension of a nucleotide. The term "ligatably adjacent to" means that two nucleotides are immediately adjacent to one another on a strand with no intervening nucleotides.

The term "tailed", in the context of a tailed oligonucleotide or a oligonucleotide that has a 5' tail or 3' tail, refers to an oligonucleotide that has a region (e.g., a region of at least 12-50 nucleotides) at its 5' or 3' end that does not hybridize to the same sequence as the other end of the primer.

The term "distinguishable sequences" refers to sequences that are different to one another.

The term "target nucleic acid" as use herein, refers to a polynucleotide of interest under study.

The term "target nucleic acid molecule" refers to a single molecule that may or may not be present in a composition with other target nucleic acid molecules. An isolated target nucleic acid molecule refers to a single molecule that is present in a composition that does not contain other target nucleic acid molecules.

The term "region" refers to a sequence of nucleotides that can be single-stranded or double-stranded.

The term "variable", in the context of two or more nucleic acid sequences that are variable, refers to two or more nucleic acids that have different sequences of nucleotides relative to one another. In other words, if the polynucleotides of a population have a variable sequence, then the nucleotide sequence of the polynucleotide molecules of the population varies from molecule to molecule. The term "variable" is not to be read to require that every molecule in a population has a different sequence to the other molecules in a population.

The term "transposon recognition sequence" refers to a double-stranded sequence to which a transposase (e.g., the Tn5 transposase or variant thereof) binds, where the transposase catalyzes simultaneous fragmentation of a double-stranded DNA sample and tagging of the fragments with sequences that are adjacent to the transposon end sequence (i.e., by "tagmentation"). Methods for tagmenting, as well as transposon end sequences, are well known in the art (see, e.g., Picelli et al, Genome Res. 2014 24: 2033-40; Adey et al, Genome Biol. 2010 11:R119 and Caruccio et al, Methods Mol. Biol. 2011 733: 241-55, US20100120098 and US20130203605). Kits for performing tagmentation are commercially sold under the tradename NEXTERA™ by Illumina (San Diego, Calif.). The Tn5 transposon recognition sequence is 19 bp in length, although many others are known and are typically 18-20 bp, e.g., 19 bp in length.

The term "adaptor" refers to a nucleic acid that can be joined, via a transposase-mediated reaction, to at least one strand of a double-stranded DNA molecule. As would be apparent, one end of an adaptor may contain a transposon end sequence. The term "adaptor" refers to molecules that are at least partially double-stranded. An adaptor may be 40 to 150 bases in length, e.g., 50 to 120 bases, although adaptors outside of this range are envisioned.

The term "adaptor-tagged," as used herein, refers to a nucleic acid that has been tagged by an adaptor. An adaptor can be joined to a 5' end and/or a 3' end of a nucleic acid molecule.

The term "tagged DNA" as used herein refers to DNA molecules that have an added adaptor sequence, i.e., a "tag" of synthetic origin. An adaptor sequence can be added (i.e., "appended") by a transposase.

Figure 3:
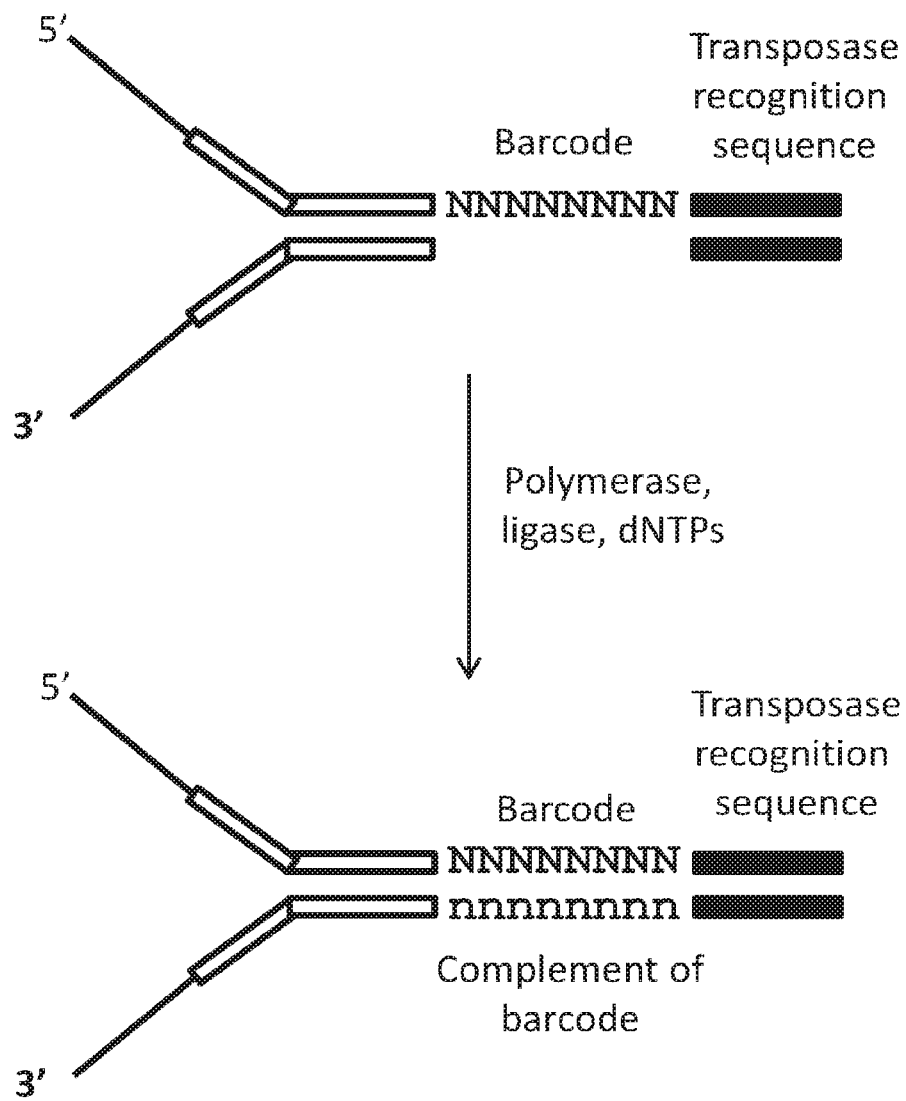
FIG. 3 schematically illustrates how a barcode can be copied from one strand to the other in the present adaptor, thereby allowing the same barcode to be added to both strands during tagmentation.

The term "Y-adaptor" refers to an adaptor that contains: a double-stranded region and a single-stranded region in which the opposing sequences are not complementary. The end of the double-stranded region may be or can be joined to target molecules such as double-stranded fragments of genomic DNA, e.g., by via a transposase-catalyzed reaction. Each strand of an adaptor-tagged double-stranded DNA that has been joined to a Y adaptor is asymmetrically tagged in that it has the sequence of one strand of the Y-adaptor at one end and the other strand of the Y-adaptor at the other end. Amplification of nucleic acid molecules that have been joined to Y-adaptors at both ends results in an asymmetrically tagged nucleic acid, i.e., a nucleic acid that has a 5' end containing one tag sequence and a 3' end that has another tag sequence. The opposing, non-complementary sequences of a Y adaptor are referred to as the "arms" of the adaptor. The double stranded region of a Y adaptor is referred to the "stem" of the adaptor. The structure of an exemplary Y adaptor is shown at the bottom of FIG. 3.

The term "an end comprising sequences that are non-complementary" refers to an end of an at least partially double-stranded molecule in which the opposing strands do not base pair with each other.

The term "complexity" refers the total number of different sequences in a population. For example, if a population has 4 different sequences then that population has a complexity of 4. A population may have a complexity of at least 4, at least 8, at least 16, at least 100, at least 1,000, at least 10,000 or at least 100,000 or more, depending on the desired result.

The term "tagmenting" as used herein refers to the transposase-catalyzed combined fragmentation of a double-stranded DNA sample and tagging of the fragments with sequences that are adjacent to the transposon end sequence. Methods for tagmenting are well known as are (see, e.g., Picelli et al, Genome Res. 2014 24: 2033-40; Adey et al, Genome Biol. 2010 11:R119 and Caruccio et al, Methods Mol. Biol. 2011 733: 241-55, US20100120098 and US20130203605). Kits for performing tagmentation are commercially sold by a variety of manufacturers.

The term "loaded' refers to a process by which a transposase and molecule containing a transposon end sequence are mixed together to form complexes that contain the transposase bound to the molecule.

The term "filling in and sealing" refers to a reaction in which a single-stranded region between two double-stranded sequences is filled in by the action of a polymerase, usually a non-strand displacing polymerase, and joined by a ligase.

The term "same barcode on both strands" and grammatical equivalents thereof refers to a double stranded molecule that has a barcode sequence covalently linked at the 5' end of one strand and the complement of the barcode sequence covalently linked at the 3' end of the other strand.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Provided herein are various compositions, methods and kits for tagging samples containing double stranded DNA molecules. The compositions, methods and kits can be employed to analyze genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, wherein in certain embodiments the mammal is a human. In exemplary embodiments, the sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, synovial fluid, urine, amniotic fluid, and semen. In particular embodiments, a sample may be obtained from a subject, e.g., a human.

In some embodiments, the sample comprises DNA fragments obtained from a clinical sample, e.g., a patient that has or is suspected of having a disease or condition such as a cancer, inflammatory disease or pregnancy. In some embodiments, the sample may be made by extracting fragmented DNA from an archived patient sample, e.g., a formalin-fixed paraffin embedded tissue sample. In other embodiments, the patient sample may be a sample of cell-free circulating DNA from a bodily fluid, e.g., peripheral blood. The DNA fragments used in the initial steps of the method should be non-amplified DNA that has not been denatured beforehand. In other embodiments, the DNA in the sample may already be partially fragmented (e.g., as is the case for FFPE samples and circulating cell-free DNA (cfDNA), e.g., ctDNA).

With reference to FIG. 1, the present adapter may comprising a population of first oligonucleotides 1, a second oligonucleotide 3 and a third oligonucleotide 5, wherein the first oligonucleotides, the second oligonucleotide and the third oligonucleotide are hybridized together to produce a complex 2 that comprises: (i) a first end comprising a transposase recognition sequence 4, (ii) a central single-stranded region of variable sequence 6 and (iii) a second end comprising sequences that are non-complementary 8. In many embodiments, the first oligonucleotides should have at least 10 base pairs of complementarity with each of the second and third oligonucleotides although, in practice, the first oligonucleotides may have at least 15 base pairs of complementarity with each of the second and third oligonucleotides, as shown.

Figure 2:
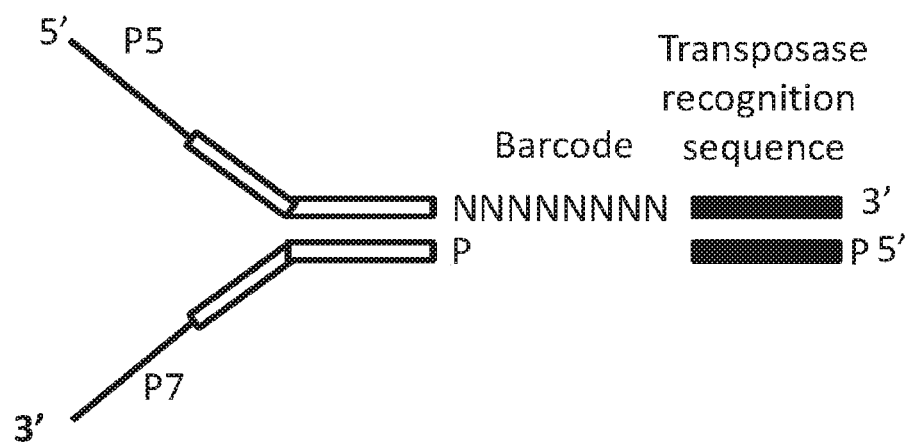
FIG. 2 schematically illustrates an embodiment of the present adaptor.
Figure 5:
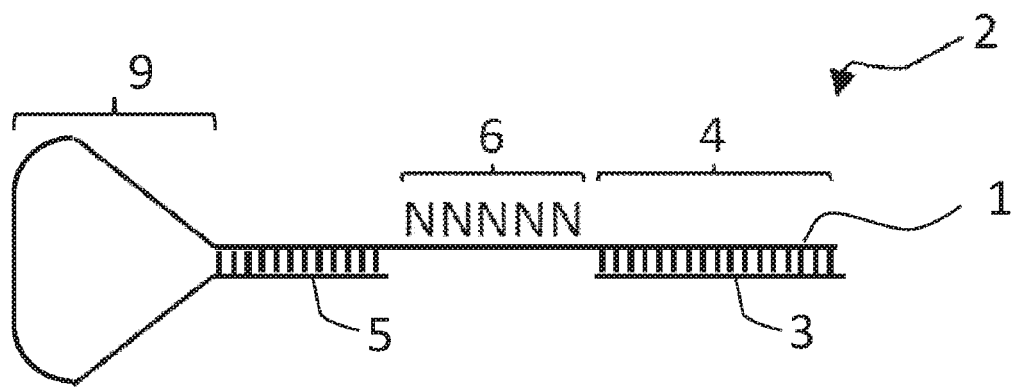
FIG. 5 schematically illustrates another embodiment of the present adaptor, wherein the single stranded regions are joined to form a loop region.

In some embodiments, the non-complementary sequences 8, i.e., the "arms", may be of any suitable length, e.g., at least 10, at least 12, at least 14 nucleotides in length, and may be designed to be compatible with the sequencing platform being used downstream. For example, as shown in FIG. 2, the adaptor may contain P5 and P7 sequences, which are compatible with Illumina's sequencing platform. In some embodiments, as shown in FIG. 5, the non-complementary sequences may be joined to one another in a loop structure 9. The variable sequence 6 may be at least 2, e.g., at least 3, at least 4, at least 5, at least 6, at least 7 or at least 8 nucleotides in length, and may have a complexity of at least 4, at least 8, at least 16, at least 100, at least 1,000, at least 10,000 or more, depending on how the variable sequence will be used. The top strand of the complex shown in FIG. 2 may be in the 5' to '3 orientation or the 3' to 5' orientation.

As shown, in FIG. 2, in certain embodiments the population of first oligonucleotides comprises a 5' region, a 3' region, and a region of variable sequence between the 5' region and the 3' region; the second oligonucleotide is complementary to and hybridizes with the 3' region of the first oligonucleotides to form the transposase recognition sequence (shown in black); and the third oligonucleotide comprises 5' end that is complementary to and is hybridized with the 3' end of the 5' region of the first oligonucleotide and comprises a 3' tail that is non-complementary to the 5' end of the 5' region of the first oligonucleotide. As shown, both the second and third oligonucleotides have a 5' phosphate.

The transposase recognition sequence of the adaptor may be the transposase recognition sequence of a Tn transposase (e.g. Tn3, Tn5, Tn7, Tn10, Tn552, Tn903), a MuA transposase, a Vibhar transposase (e.g. from *Vibrio harveyi*), although the transposase recognition sequence for other transposases (Ac-Ds, Ascot-1, Bs1, Cin4, Copia, En/Spm, F element, hobo, Hsmar1, Hsmar2, IN (HIV), IS1, IS2, IS3, IS4, IS5, IS6, IS10, IS21, IS30, IS50, IS51, IS150, IS256, IS407, IS427, IS630, IS903, IS911, IS982, IS1031, ISL2, L1, Mariner, P element, Tam3, Tc1, Tc3, Tel, THE-1, Tn/O, TnA, Tn3, Tn5, Tn7, Tn10, Tn552, Tn903, Tol1, Tol2, TnlO, Tyl, including variants thereof) can also be used.

The composition containing the adaptor may also contain a transposase that recognizes the transposase recognition sequence and in certain cases the transposase may be loaded with the adaptor. The composition can also comprise a non-strand displacing polymerase (e.g., T4 DNA polymerase) and a ligase.

As will be apparent from the discussion that follows below, the variable sequence acts as a molecular barcode that helps identify the fragment as well as the strand of the fragment after sequencing. As will be explained in greater detail below (and as shown in FIG. 3), the variable region can be readily copied to the other strand of the adaptor during tagmentation, thereby providing a way to tag both strands of a fragment of DNA with the same molecular barcode. Specifically, the adaptor provides a way by which both strands of a double-stranded molecule can be tagged with the same barcode such that, after sequencing or amplification, the sequence reads derived from the top strand can be linked and/or compared to the sequence reads derived from the bottom strand. This feature is significant because "real" mutations should be in both strands (i.e., in both the top strand and the bottom strand), and knowing whether a sequence read is from the top strand or the bottom strand allows the top strand sequences to be compared with bottom strand sequences to provide more confidence that a variation in a sequence really corresponds to a mutation.

Also provided herein is a method for tagmenting a sample, comprising contacting a sample comprising double-stranded DNA with a transposase loaded with the above-described adaptor; and filling in and sealing the central single-stranded region of the adaptor using a polymerase and ligase. The properties of the DNA polymerase used for filling and sealing reaction should be carefully considered. In some embodiments, a non strand displacing polymerase is used, so the second duplex region 5 remains annealed. In other embodiments, a strand displacing polymerase may be used under conditions such that the second duplex region 5 is only displaced by a few nucleotides, and the resulting structure may be resolved by flap endonuclease activity in conjunction with a ligase activity. Examples of non-strand displacing polymerases include T4 or T7 polymerases. In some embodiments, a polymerase with reduced or absent 3'-5' exonuclease activity may be used, so that the 3' arm of the Y is not digested by the polymerase. For example, a mutant T4 polymerase with reduced 3'-5' exo activity may be used. For example, *Sulfolobus* DNA Polymerase IV may be used. This reaction produces a population of DNA fragments that are tagged at both ends by a Y adaptor each comprising the variable sequence of a first oligonucleotide on both strands. FIG. 3 schematically illustrates this fill in and sealing reaction. After this reaction, both strands of one end of a fragment will be associated with a first barcode and its complement, whereas both strands of the other end of a fragment will be associated with a second barcode and its complement. Further, because transposase insertion is directional, every fragment generated by the method will be asymmetrically tagged in that 5' end of every tagged strand of DNA will by linked to one of the non-complementary sequences of 8 (e.g., the P5 sequence) and the 3' end of the strands will be linked to the other the non-complementary sequence of 8 (e.g., the P3 sequence). Asymmetrically tagged fragments can be efficiently amplified using a pair of primers that target the non-complementary sequence (e.g., which target the P5 and p7 sequences, for example).

Figure 4:
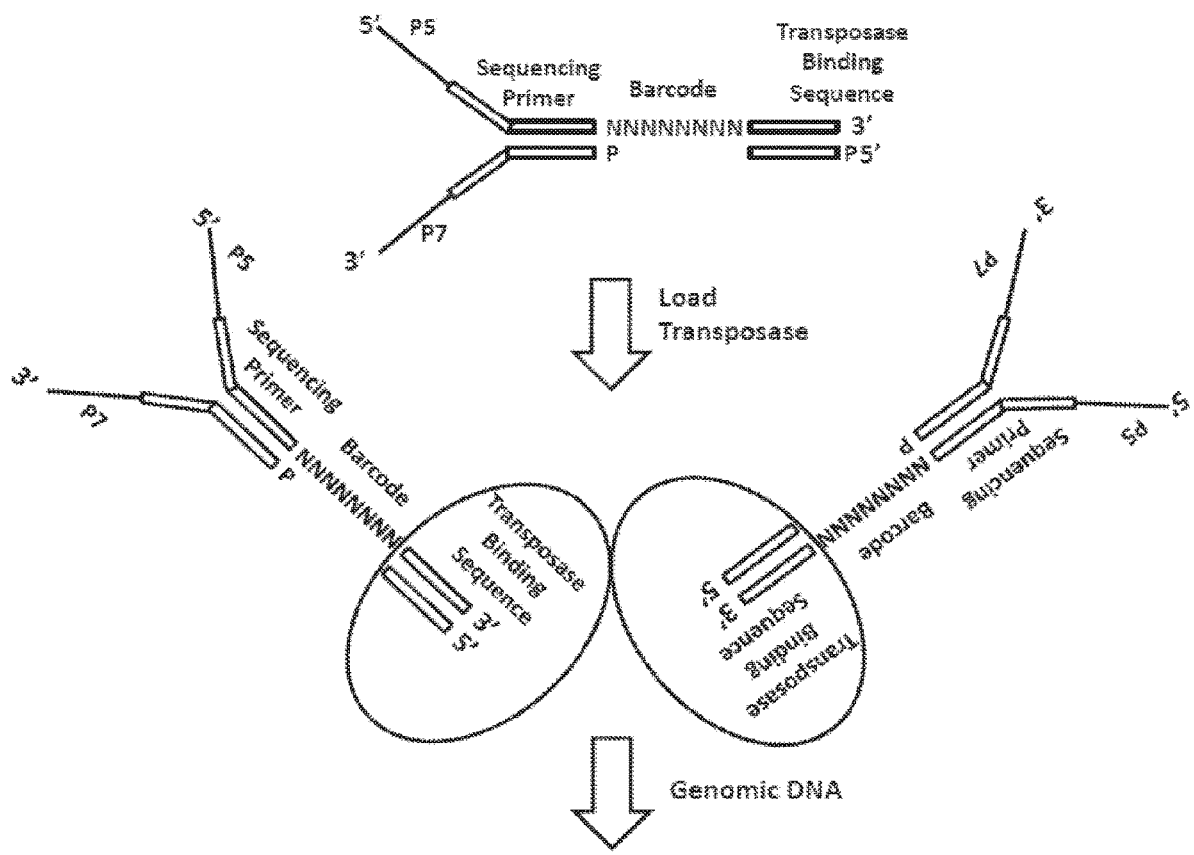
FIG. 4 schematically illustrates how the present adaptor can be used to tag genomic DNA.
Figure 4:
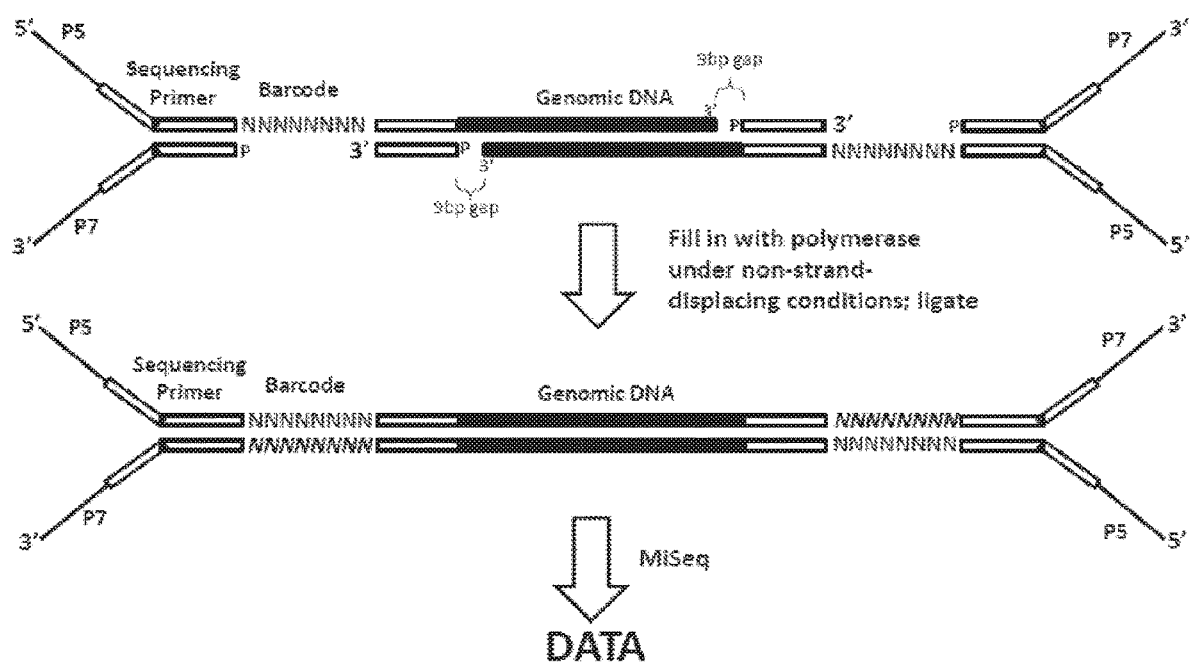

In particular embodiments, the filling and sealing reaction may be done at in the same reaction as the filling in and sealing reaction that occurs during tagmentation (and as shown in FIG. 4). As such, in some embodiments, the method may be done by combining, in a single reaction vessel, the sample, the transposase loaded with the adaptor, the polymerase (e.g., T4 DNA polymerase) and the ligase. In these embodiments, the polymerase and the ligase fill in and seal the single stranded region of the adaptor, as well as repair the gap (which is often 9 bp) that is between the 3' end of the tagged fragment and the 5' end of the bottom strand of the transposon recognition sequence.

With reference to FIG. 4, some embodiments of the method may involve loading the adaptor into a transposase dimer, and mixing the loaded adaptor with genomic DNA and other necessary reagents (e.g., dNTPs, ligase, polymerase, etc.) under conditions in which tagmentation occurs. The gaps in the resulting complex, caused by the transposase breaks and by the single-stranded barcode region, can be filled in with a non-strand displacing polymerase such as T4 DNA Polymerase, and the ends ligated with a DNA ligase, made possible by the 5' phosphates on two of the second and third oligonucleotides.

In an alternate embodiment the oligonucleotide containing the sequencing primer and the P7 sequence is hybridized to the genomic fragments after transposition rather than being loaded into the transposase before transposition. This has several potential advantages. First, it means that there will be no loss of assay efficiency due to a loss of this third piece prior to ligation, for example in storage or rehydration of the enzyme stock. Second, double-stranded DNA is a potential target for transposases during the transposition reaction. The double-stranded regions may be too short for efficient transposition, but there may be significant amount of cleavage activity. Third, its absence enables the melting away of the 19 bp phosphorylated transposase recognition sequence prior to ligation. This means that only a single ligation event is necessary per end, which may be useful depending on the efficiency of that step. These embodiments come at the expense of additional hybridization reaction. However, since the hybridized stem sequence can be identical for all ends, that hybridization reaction can be done in excess and relatively fast.

Figure 6A:
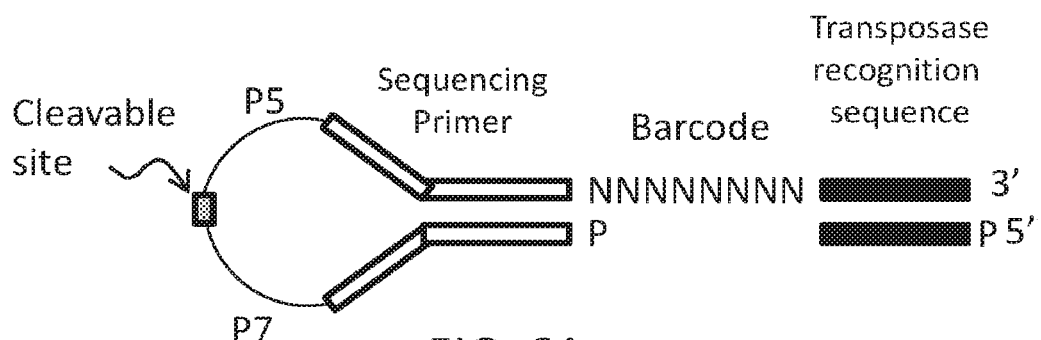
FIGS. 6A, 6B, and 6C schematically illustrate other embodiments of the present adaptor, wherein the loop region comprises a cleavage site.
Figure 6B:
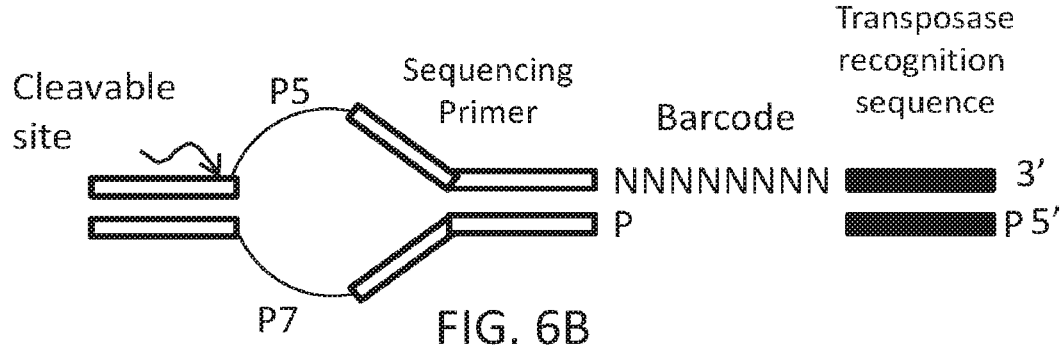
Figure 6C:
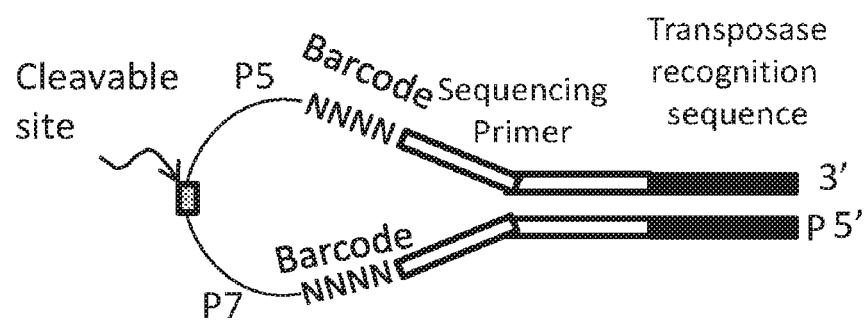
Figure 7:
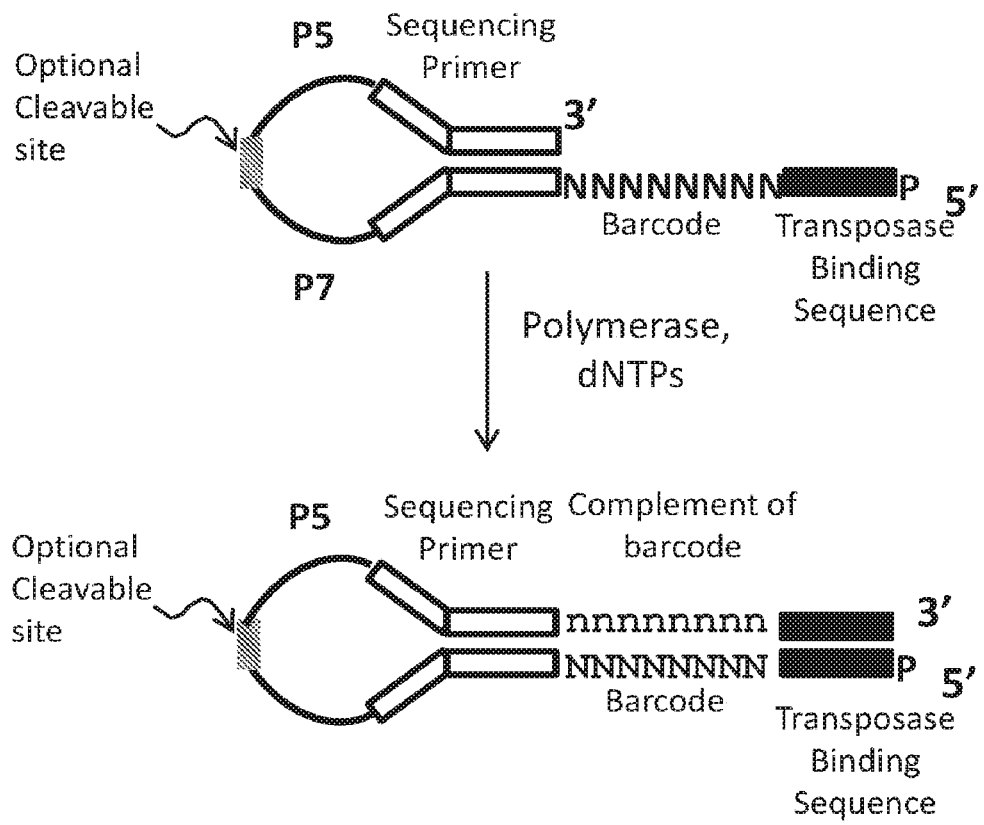
FIG. 7 schematically illustrates how another embodiment of the present adaptor can be constructed, allowing the same barcode to be added to both strands during tagmentation.

In some embodiments, the adapter may comprise only one or two molecules which form a stem-loop structure, with a duplex region comprising the transposase recognition sequence (FIG. 5, shown in black), and a single-stranded loop region (FIG. 5). One example of transposase adapters using stem loop adapters is described in US Patent Application 2010/0120098 A1. However, in the embodiments we describe here, we use large loop regions comprising specific amplification sequences. One advantage of this looped configuration is that the single-stranded regions of the adaptor will be resistant to exonuclease digestion, or the 3'-5' exonuclease activity present in some polymerases. A second advantage of this configuration is that only one or two oligonucleotides are needed to form the adaptor, instead of three. In embodiments, a single long oligonucleotide the loop region may have a cleavable region, such as a region of ribonucleic acid subject to cleavage by ribonucleases, or one or more deoxyuridine residues, subject to cleavage by the USER enzyme, or one or more abasic sites, or a chemically cleavable or photocleavable group (FIG. 6A). In other embodiments, the cleavable region may comprise another duplex region comprising a restriction digestion site. The duplex region may be formed by using sequences which allow the single stranded regions to anneal at their ends (FIG. 6B) or by using a splint oligonucleotide which anneals to both of the ends of the single stranded regions of the adaptor. Use of stem loop structures as adaptors is described in U.S. Pat. Nos. 8,883,990, 8,029,993, and 8,288,097. In other embodiments, the single-stranded loop region may also contain one or more sequences of random nucleotides (DBR), which may act as unique molecular identifiers (FIG. 6C). In these embodiments, the entire adaptor may be made from a single oligonucleotide annealed to itself, and the filling in and sealing step will only need to seal the 9 base gap created by the transposition reaction. Additionally, the use of a single loop structure in place of the arms of the Y will enable an alternative method of adaptor construction (FIG. 7.) In this embodiment, the adaptor can be constructed using a single oligonucleotide, and primer extension by a polymerase will copy the DBR barcode and the transposase binding site. These extended adaptors can then be loaded into the transposase enzyme for tagmentation, and as in FIG. 6C, the filling and sealing reaction will only need to seal the 9 base gap created by the transposase reaction.

In some embodiments, there is no cleavable region in the single stranded loop. In these embodiments, the filling and sealing reaction on the loop adaptors will convert the duplex target DNA into a circular DNA. Methods for working with and sequencing circular DNA targets have been described in Travers K J et al., Nucleic Acids Res. 2010 August; 38(15): e159, and some of these methods have been commercialized as the SMRTbell technology by Pacific Biosciences Corporation. In the embodiments described here, after tagmentation with stem loop adaptors, the circular DNA product that is formed can be resolved to a linear product after amplification by PCR, using primers which bind within the loop.

Figure 8:
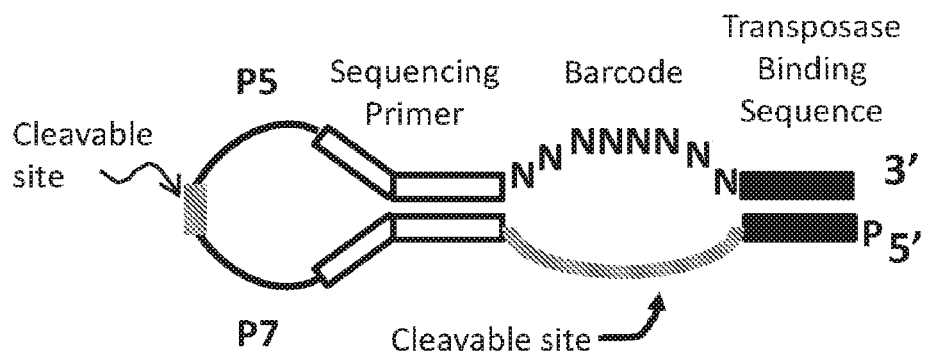
FIG. 8 schematically illustrates an adaptor with single stranded regions comprising cleavable sites and degenerate base region (DBR) barcode denoted as "NNN."

FIG. 8 illustrates another embodiment of the adaptor, wherein there are multiple single stranded regions comprising cleavage sites. In this Figure, P5 and P7 represent primer sequences necessary for bridge amplification on the Illumina platform; these could be replaced by corresponding sequences for another sequencing platform, e.g., Ion Torrent; "P" indicates 5' phosphorylation, and Transposase binding sequence (shown in black) is the 19 bp ES sequence. In embodiments, the single stranded region opposite from the DBR (gray) may comprise one or more clevable sites. For example, the region opposite the DBR may comprise ribonucleic acid subject to cleavage by ribonucleases, or one or more deoxyuridine residues, subject to cleavage by the USER enzyme, or one or more abasic sites, or one or more chemically cleavable or photocleavable groups. The cleavage sites opposite the DBR and the cleavage site in the single stranded loop may be cleaved by the same method, or may be cleaved by different methods.

In other embodiments, adaptor structures other than the "Y" adaptor in FIG. 1 or the stem loop adaptor in FIG. 5 are envisioned. For example, if the Y adaptor is formed by annealing two or three oligonucleotide molecules, as shown schematically in FIG. 1, one or both single stranded regions of the Y may comprise palindromic sequences which fold back onto themselves, creating a hairpin and the 3' end, the 5' end, or both. This hairpin strategy may be useful to reduce or eliminate digestion of the single stranded regions by exonuclease activity, particular the strong 3'-5' exonuclease activity found in some DNA polymerases such as T4 DNA polymerase or T7 DNA polymerase. Alternatively, the linkages of the Y adaptor may comprise 3'-3' linked nucleotides, or phosphothioate linkages, rendering them nuclease resistant.

In any embodiment the method may further comprise amplifying the population of tagged DNA fragments using primers that hybridize or are complementary to the arms of the Y adaptor (i.e., using one primer that is complementary to the sequence added to one end of each strand and another primer that is the same as a sequence added to the other end of the strand). As noted above, because the fragments that result from this process are asymmetrically tagged, this part of the method is at least twice as efficient as methods in which two different adaptors are used. This amplification step may be done in solution (i.e., using primers that are in solution) or it may be done by bridge PCR (using primers, e.g., P5 and P7 primers that are tethered to a solid support). As such, in certain cases the tagmented product may be applied directly to the substrate used for sequencing and amplified by bridge PCR. As would be apparent, if the fragments are to be sequenced without amplification in solution, then the arms of the adaptor should be compatible with the sequencing platform being used, e.g., Illumina's reversible terminator method, Roche's pyrosequencing method (454), Life Technologies' sequencing by ligation (the SOLiD platform) or Life Technologies' Ion Torrent platform, etc. In other embodiments, the tagged may be amplified in solution prior to sequencing, in which case other primers (e.g., primers that are tailed with P5 and P7 sequences) may be used. In other words, the tagged DNAs can either be purified and loaded directly onto the Illumina sequencing chip, or subject to PCR with the P5 and P7 primer sequences to generate more target material, if desired. The resulting tagmented DNA should represent 100% of the genomic DNA starting sequences, and thus levels of allelic dropouts may be minimized. It should be noted that this method could be used without barcoding if that is not required. Other NGS methods that do not utilize the P5 and P7 sequences could also be used with this method, by modifying the initial adapter sequences accordingly.

Next, at least some of the tagged DNA fragments may be sequenced. The tagged fragments may be sequenced directly or, in some embodiments, the fragments may be amplified (e.g., by PCR) to produce amplification products and then sequenced. Examples of next generation sequencing methods are described in the following references: Margulies et al (Nature 2005 437: 376-80); Ronaghi et al (Analytical Biochemistry 1996 242: 84-9); Shendure et al (Science 2005 309: 1728-32); Imelfort et al (Brief Bioinform. 2009 10:609-18); Fox et al (Methods Mol Biol. 2009; 553:79-108); Appleby et al (Methods Mol Biol. 2009; 513:19-39) and Morozova et al (Genomics. 2008 92:255-64), which are incorporated by reference for the general descriptions of the methods and the particular steps of the methods, including all starting products, reagents, and final products for each of the steps.

The sequencing step may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads. The products may be sequenced using any suitable method including, but not limited to Illumina's reversible terminator method, Roche's pyrosequencing method (454), Life Technologies' sequencing by ligation (the SOLiD platform), Life Technologies' Ion Torrent platform or Pacific Biosciences' fluorescent base-cleavage method. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps.

In another embodiment, the tagged DNA may be sequenced using nanopore sequencing (e.g., as described in Soni et al. Clin. Chem. 2007 53: 1996-2001, or as described by Oxford Nanopore Technologies). Nanopore sequencing is a single-molecule sequencing technology whereby a single molecule of DNA is sequenced directly as it passes through a nanopore. A nanopore is a small hole, of the order of 1 nanometer in diameter. Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Nanopore sequencing technology is disclosed in U.S. Pat. Nos. 5,795,782, 6,015,714, 6,627,067, 7,238,485 and 7,258,838 and U.S. Pat Appln Nos. 2006003171 and 20090029477.

The molecular barcode sequence may be identified in the sequence reads, and used to identify sequence errors, for allele calling, for assigning confidence, to perform copy number analysis and to estimate gene expression levels using methods that can be adapted from known methods, see, e.g., Casbon (Nucl. Acids Res. 2011 39: e81), Fu (Proc. Natl. Acad. Sci. 2011 108: 9026-9031) and Kivioia (Nat. Methods 2011 9: 72-74). If an error correctable barcode is used, then such analyses may become more accurate because, even if one barcode is mis-read, the error can be corrected or the read can be eliminated.

The sequence reads may be analyzed by a computer and, as such, instructions for performing the steps set forth below may be set forth as programing that may be recorded in a suitable physical computer readable storage medium. The general principles of some of the analysis steps are described below.

As noted above, the method results in the same barcode sequence (i.e., a barcode sequence and its complement) being appended to both strands of a fragment, which allow one to match reads that are derived from the top strand of an initial fragment from reads that are derived from the bottom strand of that fragment. In some cases, the barcode sequences may be seen at the beginning of the sequence read or at the end of the sequence read. In certain cases, a distal barcode may be identified at the beginning of a paired end sequence read.

In some implementations, the sequence reads may undergo initial processing to identify any molecular barcodes in the sequence (including sample identifier sequences), and/or trimming reads to remove low quality or unnecessary adaptor sequences. In some embodiments, the sequence reads may be grouped by their sequence and fragmentation breakpoints of the sequence read, where a fragmentation breakpoint is represented by the "end" of the sequence after the added sequences have been trimmed off. Assuming the breaks are at random or semi-random positions, different fragments having the same sequence can be distinguished by their fragmentation breakpoints. Grouping the sequence reads by their fragmentation breakpoints provides a way to determine if a sequence (e.g., a variant) is present in more than one starting molecule.

In certain embodiments, the method may further comprise identifying a potential sequence variation in a group of sequence reads that correspond to the top strand of a fragment and determining if the potential sequence variation is in any of the sequence reads that correspond to the bottom strand of the fragment. These reads can be grouped because, as noted above, they share the same barcode. If a potential sequence variation is not in both strands of the fragment, it is more likely than not that the potential sequence variation is due to a PCR or sequencing error. If a potential sequence variation is in both strands of the fragment, it is more likely than not that the potential sequence variation corresponds to a "real" sequence variation in the sample. The confidence that a potential sequence variation is a true variation (rather than a PCR or sequencing error) therefore increases if it is present in both strands of the same molecule in sample. The ability to distinguish between sequence reads that are derived from different fragments and sequence reads that are derived from different strands of the same fragment allows one to determine whether a sequence variation is real with more confidence.

In certain embodiments, the sample sequenced may comprise a pool of nucleic acids from a plurality of samples, wherein the nucleic acids in the sample have a different molecular barcode to indicate their source. In some embodiments the nucleic acids being analyzed may be derived from a single source (e.g., from different sites or a timecourse in a single subject), whereas in other embodiments, the nucleic acid sample may be a pool of nucleic acids extracted from a plurality of different sources (e.g., a pool of nucleic acids from different subjects), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. These molecular barcodes allow the sequences from different sources to be distinguished after they are analyzed. Such barcodes may be in the adaptor, or they may be added the amplification process (after tagging).

Kit

Also provided by this disclosure are kits for practicing the subject method, as described above. In certain embodiments, the kit may comprise a transposase and an adaptor as described above. In some embodiments, the kit may further comprise a ligase and polymerase and, in certain embodiments, the transposase is loaded with the adaptor. The loaded transposase, polymerase, and ligase may be in a mix, i.e., in a single vessel. In some embodiments, the kit further comprises a pair of primers that are complementary to or the same as the non-complementary sequences at the second end of the adaptor.

Either of the kits may additionally comprise suitable reaction reagents (e.g., buffers etc.) for performing the method. The various components of the kit may be present in separate containers or certain compatible components may be precombined into a single container, as desired. In addition to the reagents described above, a kit may contain any of the additional components used in the method described above, e.g., one or more enzymes and/or buffers, etc.

In addition to above-mentioned components, the subject kits may further include instructions for using the components of the kit to practice the subject methods, i.e., to instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLE

Genomic DNA was successfully tagmented and sequenced using Vibhar transposase loaded with Y adapter oligonucleotides in the following manner. We first annealed two oligonucleotides with the following sequences:

(SEQ ID NO: 1)
5'-AAGAACCAGGCTTGTCCTCA<u>TAGATCGC</u>ACTTGTGATCAAGAGACAG-3' and (SEQ ID NO: 2)
5'-pCTGTCTCTTGATCACAAGT<u>TAAGGCGA</u>TTTCTCAAGGCAATGGGACT-3'

Annealing was performed by resuspending the lyophilized oligonucleotides to a concentration of 800 micromolar in a solution of 10 mM bicine (pH 7.9) and 20 mM KCl. The two oligonucleotides were then mixed in a one-to-one ratio and heated to 70 degrees Celsius for 10 minutes, then allowed to slowly cool to room temperature for several hours. The resulting double-stranded DNA was then bound to the Vibhar transposase by creating 50 microliters of the following mixture:

116 µM DNA
225 mM KCl
9.4% glycerol
1 mM EDTA
2 mM DTT
0.05% Igepal
3.07 mg/ml Vibhar transposase The mixture was incubated at 25 degrees Celsius for 4 hours, then at 4 degrees Celsius for three days. 4 µl of this loaded transposase mixture was then diluted by adding 118.8 µl of [20 mM bicine-NH$_4$, pH 7.9; 250 mM KCl; 2 mM DTT; 0.1 mM EDTA, pH8.0; 50% glycerol].

To tagment human genomic DNA, 1 µl of the above transposase dilution was added to 2 µl of 25 ng/µ human genomic DNA in 17 µl of Agilent SureSelect QXT Buffer from the Agilent SureSelect QXT Library Prep Kit (Agilent Technologies, catalog number G9682A). Tagmentation and subsequent purification on AMPure XP beads (Beckman Coulter Genomics catalog number A63880) was performed as described in the SureSelect QXT Library Prep Kit protocol. The nine nucleotide gap in the transposase tagmented DNA was then filled-in and ligated in the following reaction for 10 minutes at 30 degrees Celsius:

10 µl Tagmented genomic DNA
1 mM ATP
0.1 mM deoxynucleotide triphosphates
20 mM Tris-HCl
10 mM (NH4)2SO4
10 mM KCl
2 mM MgSO4
0.1% Triton X-100
2 units *Sulfolobus* DNA Polymerase IV (New England BioLabs)

3,000 units T3 DNA Ligase (New England BioLabs)

Reactions were again purified on AMPure beads and subsequently amplified by PCR as described in the Agilent SureSelect QXT Library Prep Kit protocol, except that 10 rounds of PCR were performed using the following PCR primers:

(SEQ ID NO: 3)
5'-AATGATACGGCGACCACCGAGATCTACACCGACAGGTTCAGAAGAAC

CAGGCTTGTCCTCA-3'

(SEQ ID NO: 4)
5'-CAAGCAGAAGACGGCATACGAGATGCGCGTCCGACGAGCAGTCCCAT

TGCCTTGAGAAA-3'

Analysis of the PCR reaction products with the Agilent Bioanalyzer and by sequencing on the Illumina MiSeq instrument validated that the genomic DNA was successfully tagmented and readily sequencable.

EMBODIMENTS

Embodiment 1: An adapter comprising a population of first oligonucleotides, a second oligonucleotide and a third oligonucleotide, wherein the first oligonucleotides, the second oligonucleotide and the third oligonucleotide are hybridized together to produce a complex that comprises: (i) a first end comprising a transposase recognition sequence, (ii) a central single-stranded region of variable sequence and (iii) a second end comprising sequences that are non-complementary.

Embodiment 2: In some embodiments a) the population of first oligonucleotides comprise a 5' region, a 3' region, and a region of variable sequence between the 5' region and the 3' region; b) the second oligonucleotide is complementary to and hybridizes with the 3' region of the first oligonucleotides to form the transposase recognition sequence; and c) the third oligonucleotide comprises 5' end that is complementary to and is hybridized with the 3' end of the 5' region of the first oligonucleotide and comprises a 3' tail that is non-complementary to the 5' end of the 5' region of the first oligonucleotide.

Embodiment 3: The adaptor of any prior embodiment, wherein the variable sequence has a complexity of at least 10.

In any embodiment, the 5' end of the first oligonucleotide and the 3' tail of the third oligonucleotide may be joined together by a cleavable region.

Embodiment 4: The adaptor of any prior embodiment, wherein the variable sequence has a complexity of at least 1,000.

In any embodiment, the first, second, and third oligonucleotides may be formed by allowing self-annealing of a single oligonucleotide of greater than 60 nucleotides, followed by cleavage of cleavable sites located between the sequences between the first and third oligonucleotides and between the sequences of the second and third oligonucleotide.

Embodiment 5: The adaptor of any prior embodiment, wherein the transposase recognition sequence is the recognition sequence for a Tn5 transposase or variant thereof.

Embodiment 6: The adaptor of any prior embodiment, wherein the transposase recognition sequence is the recognition sequence for a Vibhar transposase or variant thereof.

Embodiment 7: The adaptor of any prior embodiment, wherein the first oligonucleotides have at least 10 base pairs of complementarity with each of the second and third oligonucleotides.

In any embodiment, the 3' tail of the third oligonucleotide may comprises a modification rendering the 3' end resistant to digestion by a 3'-5' exonuclease activity.

Embodiment 8: A composition comprising the adaptor of any of embodiments 1-7 and a transposase.

Embodiment 9: A method for tagmenting a sample, comprising; contacting a sample comprising double-stranded DNA with a transposase loaded with the adaptor of any of embodiments 1-7; and filling in and sealing the central single-stranded region of the adaptor using a polymerase and ligase, thereby producing a population of DNA fragments that are tagged at both ends by a Y adaptor each comprising the variable sequence of a first oligonucleotide on both strands.

Embodiment 10: The method of any prior method embodiment, wherein the method is done by combining, in a single reaction vessel, the sample, the transposase loaded with the adaptor, the polymerase and the ligase.

Embodiment 11: The method of any prior method embodiment, wherein the filling in is done by T4 polymerase.

In any embodiment, the filling may be done by *Sulfolobus* DNA polymerase IV, at a temperature less than 50 degrees Celsius.

Embodiment 12: The method of any prior method embodiment, wherein the method further comprises amplifying the population of DNA fragments using primers that target the arms of the Y adaptor.

Embodiment 13: The method of embodiment 12, wherein the amplifying is done in solution.

Embodiment 14: The method of embodiment 12, wherein the amplifying is done by bridge PCR.

Embodiment 15: The method of any prior method embodiment, further comprising sequencing at least some of the tagged DNA fragments.

Embodiment 16: The method of any prior method embodiment, further comprising sequencing at least some of the tagged DNA fragments.

Embodiment 17: The method of any prior method embodiment, wherein a) the population of first oligonucleotides comprise a 5' region, a 3' region, and a region of variable sequence between the 5' region and the 3' region; b) the second oligonucleotide is complementary to and hybridizes with the 3' region of the first oligonucleotides to form the transposase recognition sequence; and c) the third oligonucleotide comprises 5' end that is complementary to and is hybridized with the 3' end of the 5' region of the first oligonucleotide and comprises a 3' tail that is non-complementary to the 5' end of the 5' region of the first oligonucleotide.

Embodiment 18: The method of any prior method embodiment, wherein the variable sequence has a complexity of at least 10.

Embodiment 19: The method of any prior method embodiment, wherein the variable sequence has a complexity of at least 1,000.

Embodiment 20: The method of any prior method embodiment, wherein the transposase recognition sequence is the recognition sequence for a Tn5 transposase or variant thereof.

Embodiment 21: The method of any prior method embodiment, wherein the transposase recognition sequence is the recognition sequence for a Vibhar transposase or variant thereof.

Embodiment 22: The method of any prior method embodiment, wherein the first oligonucleotides have at least 10 base pairs of complementarity with each of the second and third oligonucleotides.

Embodiment 23: A kit comprising: a transposase; an adaptor of any of embodiments 1-7; and a polymerase.

Embodiment 24: The kit of any prior kit embodiment, wherein the transposase is loaded with the adaptor.

Embodiment 25: The kit of any prior kit embodiment, wherein the loaded transposase, polymerase, and ligase are in a mix.

Embodiment 26: The kit of any prior kit embodiment, wherein the kit further comprises a pair of primers that are complementary to or the same as the non-complementary sequences at the second end of the adaptor.

In some embodiments: a) the population of first oligonucleotides comprise a 5' region, a 3' region, and a region of variable sequence between the 5' region and the 3' region; b) the second oligonucleotide is complementary to and hybridizes with the 3' region of the first oligonucleotides to form the transposase recognition sequence; and c) the third oligonucleotide comprises 5' end that is complementary to and is hybridized with the 3' end of the 5' region of the first oligonucleotide and comprises a 3' tail that is non-complementary to the 5' end of the 5' region of the first oligonucleotide.

Embodiment 27: The kit of any prior kit embodiment, wherein the variable sequence has a complexity of at least 10.

Embodiment 28: The kit of any prior kit embodiment, wherein the variable sequence has a complexity of at least 1,000.

Embodiment 29: The kit of any prior kit embodiment, wherein the transposase recognition sequence is the recognition sequence for a Tn5 transposase or variant thereof.

Embodiment 30: The kit of any prior kit embodiment, wherein the transposase recognition sequence is the recognition sequence for a Vibhar transposase or variant thereof.

Embodiment 31: The kit of any prior kit embodiment, wherein the first oligonucleotides have at least 10 base pairs of complementarity with each of the second and third oligonucleotides.

Embodiment 32: An adapter comprising first oligonucleotide and a second oligonucleotide, wherein the first and second oligonucleotides are hybridized together to produce a complex that comprises: (i) a first end comprising a double stranded transposase recognition sequence and (ii) a second end comprising sequences that are non-complementary. This two oligonucleotide adaptor may contain many, if not all of the general characteristics of the three oligonucleotide adaptor described above, e.g., barcodes, etc., except that the single stranded variable regions is now double stranded and part of the stem of the adaptor. In some cases, in this embodiment, one of the arms of the adaptor may contain a barcode.

Embodiment 33: A method for tagmenting a sample, comprising; contacting a sample comprising double-stranded DNA with a transposase loaded with the adaptor of embodiment 31, thereby producing a population of DNA fragments that are tagged at both ends by a Y adaptor each comprising the variable sequence of a first oligonucleotide on both strands.

Embodiment 34: an adapter containing a first oligonucleotide, wherein the first oligonucleotide comprises: (i) a duplex region and a single stranded loop region, (ii) the duplex region comprises a transposase recognition sequence, and (iii) the single stranded loop region comprises a cleavage region.

Embodiment 35: the adapter of any prior embodiment, wherein the adapter comprises a region of variable sequence.

Embodiment 36: the adapter of any prior embodiment, wherein the adapter comprises a region of variable sequence, wherein the variable sequence is in the single-stranded region.

Embodiment 37: the adapter of any prior embodiment, wherein the adapter comprises more than one region of variable sequence, wherein the variable sequences are in the single-stranded region.

Embodiment 38: the adapter of any prior embodiment, wherein the adapter comprises more than one cleavable region, wherein one cleavable region is in the single-stranded region.

Embodiment 39: the adapter of any prior embodiment, wherein the adapter comprises deoxynucleic acid and the cleavable region comprises uracil or deoxyuracil.

Embodiment 40: the adapter of any prior embodiment, wherein the adapter comprises deoxyribonucleic acid, and the cleavable region comprises ribonucleic acid. Embodiment 41: the adapter of any prior embodiment, wherein the adapter comprises deoxyribonucleic acid, and the cleavable region comprises a chemically cleavable group.

Embodiment 42: the adapter of any prior embodiment, wherein the adapter comprises deoxyribonucleic acid, and the cleavable region comprises a photocleavable group.

Embodiment 43: the adapter of any prior embodiment, wherein the 5' end of the first oligonucleotide and the 3' tail of the third oligonucleotide are joined together by a cleavable region.

Embodiment 44: the adapter of any prior embodiment, wherein the first, second, and third oligonucleotides are formed by allowing self-annealing of a single oligonucleotide of greater than 60 nucleotides, followed by cleavage of cleavable sites located between the sequences between the first and third oligonucleotides and between the sequences of the second and third oligonucleotide.

Embodiment 45: the adapter of any prior embodiment, wherein the 3' tail of the third oligonucleotide comprises a modification rendering the 3' end resistant to digestion by a 3'-5' exonuclease activity, wherein resistant is defined as having less exonuclease digestion than native, single stranded DNA without modifications.

Embodiment 46: The method of any prior method embodiment, wherein the filling in is done by a T4 polymerase mutant with reduced or absent 3'-5' exonuclease activity.

Embodiment 47: The method of any prior method embodiment, wherein the filling in is done by a T7 polymerase mutant with reduced or absent 3'-5' exonuclease activity.

Embodiment 48: The method of any prior method embodiment, wherein the filling in is done by a *Sulfolobus* DNA polymerase.

Embodiment 49: The method of any prior method embodiment, wherein the filling in is done by a *Sulfolobus* DNA polymerase, at a temperature less than 50 degrees Celsius.

The invention claimed is:

1. A method for tagmenting a sample, comprising:
   contacting a sample comprising double-stranded DNA with a transposase loaded with adapters;
   wherein the adapters comprise a population of first oligonucleotides, a second oligonucleotide and a third oligonucleotide, wherein the first oligonucleotides, the second oligonucleotide and the third oligonucleotide are hybridized together to produce a complex that comprises: (i) a first end comprising a transposase recognition sequence, (ii) a central single-stranded region of variable sequence and (iii) a second end comprising sequences that are non-complementary; and
   filling in and sealing the central single-stranded region of the adaptor using a polymerase and ligase, thereby producing a population of DNA fragments that are tagged at both ends by a Y adaptor each comprising the variable sequence of a first oligonucleotide on both strands.

2. The method of claim 1, wherein the method is done by combining, in a single reaction vessel, the sample, the transposase loaded with the adaptors, the polymerase and the ligase.

3. The method of claim 1, wherein the filling in is done by *Sulfolobus* DNA polymerase IV, at a temperature less than 50 degrees Celsius.

4. The method of claim 1, wherein the method further comprises amplifying the population of DNA fragments using primers that target a non-complementary sequence of the Y adaptor.

5. The method of claim 4, wherein the amplifying is done in solution.

6. The method of claim 4, wherein the amplifying is done by bridge PCR.

7. The method of claim 1, further comprising sequencing at least some of the tagged DNA fragments.

8. The method of claim 1, wherein the variable sequence has a complexity of at least 1,000.

9. The method of claim 1, wherein the first, second, and third oligonucleotides are formed by allowing self-annealing of a single oligonucleotide molecule of greater than 60 nucleotides, followed by cleavage of cleavable sites located between the first and third oligonucleotides and between the second and third oligonucleotide.

10. The method of claim 1, wherein the transposase recognition sequence is a recognition sequence for a Vibhar transposase.

11. The method of claim 1, wherein:
a) the population of first oligonucleotides comprise a 5' region, a 3' region, and a region of variable sequence between the 5' region and the 3' region;
b) the second oligonucleotide is complementary to and hybridizes with the 3' region of the first oligonucleotides to form the transposase recognition sequence; and
c) the third oligonucleotide comprises a 5' end that is complementary to and is hybridized with the 3' end of the 5' region of the first oligonucleotide and comprises a 3' tail that is non-complementary to the 5' end of the 5' region of the first oligonucleotide.

12. The method of claim 11, wherein the 5' end of the first oligonucleotide and the 3' tail of the third oligonucleotide are in a single molecule and joined together by a cleavable region.

13. The method of claim 11, wherein the 3' tail of the third oligonucleotide comprises a modification rendering the 3' end resistant to digestion by a 3'-5' exonuclease activity.

* * * * *

SEQUENCE LISTING

```
<160> NUMBER OF SEQ ID NOS: 4

<210> SEQ ID NO 1
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 1
aagaaccagg cttgtcctca tagatcgcac ttgtgatcaa gagacag            47

<210> SEQ ID NO 2
<211> LENGTH: 47
<212> TYPE: DNA
<213> ORGANISM: artificial sequence
<220> FEATURE:
<223> OTHER INFORMATION: synthetic oligonucleotide

<400> SEQUENCE: 2
ctgtctcttg atcacaagtt aaggcgattt ctcaaggcaa tgggact            47

<210> SEQ ID NO 3
<211> LENGTH: 61
<212> TYPE: DNA
<213> ORGANISM: artificial sequence
<220> FEATURE:
<223> OTHER INFORMATION: synthetic oligonucleotide

<400> SEQUENCE: 3
aatgatacgg cgaccaccga gatctacacc gacaggttca gaagaaccag gcttgtcctc     60
a                                                                    61

<210> SEQ ID NO 4
<211> LENGTH: 59
<212> TYPE: DNA
<213> ORGANISM: artificial sequence
<220> FEATURE:
<223> OTHER INFORMATION: synthetic oligonucleotide

<400> SEQUENCE: 4
caagcagaag acggcatacg agatgcgcgt ccgacgagca gtcccattgc cttgagaaa      59
```